US007644594B2

(12) United States Patent
Berry et al.

(10) Patent No.: US 7,644,594 B2
(45) **Date of Patent: *Jan. 12, 2010**

(54) METHOD AND APPARATUS FOR SELF-CONTAINED ANESTHETIC GAS RECLAMATION

(75) Inventors: James M. Berry, Nashville, TN (US); Steve Morris, Canton, MS (US)

(73) Assignee: Anesthetic Gas Reclamation, L.L.C., Nashville, TN (US)

( * ) Notice: Subject to any disclaimer, the term of this patent is extended or adjusted under 35 U.S.C. 154(b) by 354 days.

This patent is subject to a terminal disclaimer.

(21) Appl. No.: 11/432,192

(22) Filed: May 11, 2006

(65) Prior Publication Data

US 2006/0254590 A1 Nov. 16, 2006

Related U.S. Application Data

(60) Provisional application No. 60/680,644, filed on May 13, 2005.

(51) Int. Cl.
*F25J 3/00* (2006.01)
*B01D 9/04* (2006.01)
*F24F 5/00* (2006.01)

(52) U.S. Cl. ............................ 62/617; 62/637; 62/532; 128/204.16; 128/205.12

(58) Field of Classification Search .................. 62/637, 62/617, 532; 128/200.24, 200.16, 203.25, 128/205.12; 423/235
See application file for complete search history.

(56) References Cited

U.S. PATENT DOCUMENTS 575,714 A 1/1897 Heinzerling (Continued)

FOREIGN PATENT DOCUMENTS

WO WO 98/08583 3/1998

(Continued)

OTHER PUBLICATIONS

R. F. Dunn, M. Zhu, B.K. Srinivas and M. M. El-Halwagi (1995), Optimal Design of Energy-Induced Separation Networks for VOC Recovery, *AIChE Symp. Ser.*, 90(303), 74-85, NY: AIChE.

(Continued)

*Primary Examiner*—William C Doerrler
(74) *Attorney, Agent, or Firm*—Gary L. Bush; Mark D. Shelley, II; Andrews Kurth LLP

(57) ABSTRACT

A method and apparatus are disclosed for recovering and separating anesthetic gas components from waste anesthetic gases to be purged from a healthcare facility. With minimal reliance on the utility infrastructure and supplies of a healthcare facility, the method and apparatus needs only electrical or mechanical power, a source of waste anesthetic gases, and an atmospheric vent in order to operate. A heat exchanger/condenser, which uses a dedicated heat transfer fluid as a refrigerant, is employed to condense anesthetic gas components from the waste anesthetic gases as either liquid condensates or solid frosts. The warmed heat transfer fluid is cooled in a separate refrigeration unit and recycled back to the heat exchanger/condenser. A preferred embodiment of the invention is a self-contained, packaged unit which can be easily accommodated in a physician's office, small animal clinic, dental office or other healthcare facility requiring effective waste anesthetic gas management.

20 Claims, 6 Drawing Sheets

U.S. PATENT DOCUMENTS 1,040,886 A 10/1912 Claude
3,348,538 A 10/1967 Benzel
3,517,521 A * 6/1970 Emerson ..................... 62/637
3,592,191 A 7/1971 Jackson
3,714,942 A 2/1973 Fischel et al.
3,721,239 A 3/1973 Myers
3,800,793 A 4/1974 Marrese et al.
3,867,936 A 2/1975 Kelley
3,941,573 A 3/1976 Chapel
4,004,585 A 1/1977 Boehringer
4,127,163 A 11/1978 Reti
4,180,066 A 12/1979 Milliken et al.
4,181,508 A 1/1980 Schmid et al.
4,205,095 A 5/1980 Pike et al.
4,219,020 A 8/1980 Czajka
4,246,015 A 1/1981 Styring, Jr.
4,259,303 A 3/1981 Nakaji et al.
4,261,178 A 4/1981 Cain
4,265,239 A 5/1981 Fischer, Jr. et al.
4,281,518 A 8/1981 Muller et al.
4,291,689 A 9/1981 Hay
4,312,339 A 1/1982 Thompson, Sr.
4,378,984 A 4/1983 Cheng et al.
4,447,462 A 5/1984 Tafuri et al.
4,451,273 A 5/1984 Cheng et al.
4,527,558 A 7/1985 Hoenig
4,538,605 A 9/1985 Gedeon et al.
4,609,388 A 9/1986 Adler et al.
4,633,890 A 1/1987 Carden
4,653,493 A 3/1987 Hoppough
4,676,239 A 6/1987 Humphrey
4,755,201 A * 7/1988 Eschwey et al. .............. 62/637
4,768,347 A 9/1988 Manz et al.
4,832,042 A 5/1989 Poppendiek et al.
4,895,172 A 1/1990 Lindkvist
4,905,685 A 3/1990 Olsson et al.
4,928,685 A 5/1990 Gray
4,949,714 A 8/1990 Orr
5,033,464 A 7/1991 Dlcastilho
5,044,361 A 9/1991 Werner et al.
5,044,363 A 9/1991 Burkhart
5,046,491 A 9/1991 Derrick
5,046,492 A 9/1991 Stackhouse et al.
5,062,270 A 11/1991 Haut et al.
5,152,812 A 10/1992 Kovach
5,205,843 A 4/1993 Kaschemekat et al.
5,253,641 A 10/1993 Choate
5,311,862 A 5/1994 Blasdell et al.
5,323,623 A 6/1994 Carns et al.
5,339,642 A 8/1994 Laukhuf
5,345,928 A 9/1994 Lindkvist
5,370,110 A 12/1994 Corn
5,398,675 A 3/1995 Henkin et al.
5,419,317 A 5/1995 Blasdell et al.
5,450,728 A 9/1995 Vora et al.
5,482,033 A 1/1996 Engle et al.
5,507,282 A 4/1996 Younes
5,520,119 A * 5/1996 Eisenberg .................... 108/43
5,520,169 A 5/1996 Georgieff et al.
5,568,910 A 10/1996 Koehler et al.
5,676,133 A 10/1997 Hickle et al.
5,678,540 A 10/1997 Kock et al.
5,694,924 A 12/1997 Cewers
5,715,813 A 2/1998 Guevrekian
5,740,682 A 4/1998 Lavie
5,759,504 A 6/1998 Kanno et al.
5,769,072 A 6/1998 Olsson et al.
5,819,555 A 10/1998 Engdahl
5,928,411 A 7/1999 Falb et al.
RE36,460 E 12/1999 Klatz et al.
6,030,591 A 2/2000 Tom et al.
6,076,524 A 6/2000 Corn
6,080,226 A 6/2000 Dolan et al.
6,082,133 A 7/2000 Barclay et al.
6,131,571 A 10/2000 Lampotang et al.
6,134,914 A 10/2000 Eschwey et al.
6,158,434 A 12/2000 Lugtigheid et al.
6,206,002 B1 3/2001 Lambert
6,237,596 B1 5/2001 Bohmfalk
6,328,036 B1 12/2001 Emtell et al.
6,357,437 B1 3/2002 Jacques
6,374,635 B1 4/2002 Hayakawa et al.
6,405,539 B1 6/2002 Stach et al.
6,475,266 B2 11/2002 Hayashi et al.
6,488,028 B1 12/2002 Lambert
6,490,883 B2 12/2002 Trembley et al.
6,513,345 B1 * 2/2003 Betting et al. ................. 62/637
6,536,430 B1 3/2003 Smith
6,729,329 B2 * 5/2004 Berry .................... 128/204.16
6,736,140 B1 5/2004 Baczkowski
6,776,158 B1 8/2004 Anderson et al.
6,863,067 B2 3/2005 Loncar
2003/0185735 A1 * 10/2003 Hotta et al. .............. 423/239.1
2005/0155380 A1 7/2005 Rock
2006/0254586 A1 11/2006 Berry et al.
2006/0254587 A1 11/2006 Berry et al.
2006/0254589 A1 11/2006 Berry et al.

FOREIGN PATENT DOCUMENTS

WO WO 01/24858 4/2001

OTHER PUBLICATIONS

U.S. Appl. No. 11/266,966, filed Nov. 4, 2005, Berry et al.

Brown AC, Canosa-Mas CE, Parr AD, et al.: Tropospheric lifetimes of halogenated anaesthetics. Nature 1989; 341: 635-637.

Langbein T, Sonntag H, Trapp D, et al.: Volatile anaesthetics and the atmosphere: atmospheric lifetimes and atmospheric effects of halothane, enflurane, isoflurane, desflurane and sevoflurane. Br J Anaesth 1999; 82: 66-73.

McCulloch, A.: Letter to Editor regarding Langbein, et al. 1999 paper. Br J Anaesth 2000; 84 (4): 534-36.

Written Opinion of International Search Authority for PCT/US2006/18416 mailed on Sep. 24, 2007.

Examiner's First Choice Action mailed Jul. 17, 2008 in connection with U.S. Appl. No. 11/266,966.

Applicant's Reponse to First Office filed Nov. 17, 2008 in connection with U.S. Appl. No. 11/266,966.

Examiner's Second Office Action mailed Dec. 30, 2008 in connection with U.S. Appl. No. 11/266,966.

Examiner's First Office Action mailed Oct. 15, 2008 in connection with U.S. Appl. No. 11/432,152.

Applicant's Response to First Office Action filed Apr. 14, 2009 in collection with U.S. Appl. No. 11/432,152.

Examiner's First Office Action mailed Oct. 10, 2008 in connection with U.S. Appl. No. 11/432,189.

Applicant's Response to First Office Action filed Apr. 9, 2009 in connection with U.S. Appl. No. 11/432,189.

Applicant's Supplemental Response to First Office Action filed Apr. 10, 2009 in connection with U.S. Appl. No. 11/432,189.

Examiner's Non-Final Office Action mailed Jun. 1, 2009 in connection with U.S. Appl. No. 11/432,152.

Notice of Allowance mailed May 20, 2009 in connection with U.S. Appl. No. 11/432,189.

Notice of Allowance mailed Jul. 23, 2009 in connection with U.S. Appl. No. 11/266,966.

Applicant's Response to Non-Final Office Action filed Jun. 1, 2009 in connection with U.S. Appl. No. 11/266,966.

* cited by examiner

METHOD AND APPARATUS FOR SELF-CONTAINED ANESTHETIC GAS RECLAMATION

CROSS REFERENCE TO RELATED APPLICATION

This application is based upon provisional application 60/680,644 filed on May 13, 2005, the priority of which is claimed. On Nov. 4, 2005, Applicants filed related non-provisional application Ser. No. 11/266,966, which claims the benefit of U.S. provisional patent application 60/680,644 filed on May 13, 2005. On May 11,2006, Applicants filed related non-provisional application Ser. No. 11/432,152, which claims the benefit of U.S. provisional patent application 60/680,644 filed on May 13, 2005. On May 11, 2006, Applicants filed related non-provisional application Ser. No. 11/432,189, which claims the benefit of U.S. provisional patent applications 60/680,644 filed on May 13, 2005 and 60/682,249 filed on May 18, 2005.

BACKGROUND OF THE INVENTION

1. Field of the Invention

This invention concerns the treatment of waste anesthetic gases produced by one or more anesthesia delivery systems of a healthcare or other facility that use inhaled anesthetics for medical, dental, or veterinary purposes. In order to prevent atmospheric pollution, the invention pertains to the removal and reclamation of nitrous oxide, fluoro-ethers, and other halocarbons from a stream of waste anesthetic gases prior to its discharge to the atmosphere. In particular, this invention involves the removal and reclamation of anesthetic gases using a self-contained apparatus, which allows the removal and reclamation process by condensation to be conducted with minimal interaction with the utility systems of healthcare facilities.

2. Background Art

Anesthesia delivery systems in surgical facilities (medical, dental, and veterinary) produce significant quantities of waste anesthetic gases. Currently these gases are collected from the patients' exhalation by a dedicated or shared vacuum system. The healthcare facilities typically employ one or more centrally-located vacuum pumps to collect waste gases from individual anesthetizing locations. These vacuum pumps are usually oversized, because they are designed to collect exhaled anesthetics over a wide range of flow rates. Because these pumps operate continuously, the waste anesthetic gas suction system also entrains large amounts of surrounding room air from the anesthetizing locations, significantly diluting the waste anesthetic gases therein. At the central vacuum pump(s), the gas stream is often admixed with additional room air to futher dilute it prior to its ejection from the facility. This dilute waste anesthetic gas/air mixture is typically pumped to a location outside of the surgical facility, where it is vented to the open atmosphere.

The waste anesthetic gases are generally collected at about 20-30° C. with a relative humidity ranging between 10 to 60 percent. The average composition of the waste gases is estimated to be (in volume percent): 25-32 percent oxygen, 60-65 percent nitrogen, 5-10 percent nitrous oxide, and 0.1-0.5 percent volatile halocarbons, including fluoro-ethers, such as isoflurane, desflurane and sevoflurane. The waste anesthetic gas may also contain trace amounts of lubricating oil vapor from the vacuum pumps.

An increasingly significant source of environmental concern, waste anesthetic gas halocarbons (similar in composition to Freon-12® and other refrigerants) have been linked to ozone depletion and to a lesser degree, global warming. The halocarbons used in anesthesia (primarily halogenated methyl ethyl ethers) now represent a significant emissions source, because other industrial and commercial halocarbon emissions have been greatly reduced by legislation and other initiatives in recent years. Although waste anesthetic gas emissions have so far escaped environmental regulation in the United States, legislative initiatives to strictly regulate waste anesthetic gas emissions will likely occur in the near future.

Several techniques have been proposed to treat waste anesthetic gases in an attempt to mitigate the growing problem of waste anesthetic gas emissions. For example, U.S. Pat. No. 4,259,303 describes the treatment of laughing gas with a catalyst, U.S. Pat. No. 5,044,363 describes the adsorption of anesthetic gases by charcoal granules, U.S. Pat. No. 5,759,504 details the destruction of anesthetic gases by heating in the presence of a catalyst, U.S. Pat. No. 5,928,411 discloses absorption of anesthetic gases by a molecular sieve, and U.S. Pat. No. 6,134,914 describes the separation of xenon from exhaled anesthetic gas. A cryogenic method for scrubbing volatile halocarbons from waste anesthetic gas is disclosed by Berry in U.S. Pat. No. 6,729,329, which is incorporated herein by reference.

Another cryogenic waste anesthetic gas condensation system has recently been disclosed by Berry, et al. in co-pending application Ser. No. 11/432,189, entitled "Anesthetic Gas Reclamation System and Method." This system uses a batch-mode frost fractionation process whereby the temperatures of the individual anesthetic gases are lowered to a point such that they condense and collect as frost on the cooling surfaces of a cold trap/fractionator. This co-pending application, filed on May 11, 2006, is incorporated herein by reference.

FIG. 1 illustrates a typical waste anesthetic gas reclamation system 10 of prior art for a healthcare facility. The system 10 includes a number of individual anesthetizing stations 15A, 15E, 15C, each having an anesthetizing machine 12A, 12B, 12C which delivers anesthesia to a patient via a mask 14A, 14B, 14C or similar device. Excess anesthetic gases, patients' exhalation, and air are collected at the masks 14A, 14B, 14C by the anesthetizing machines 12A, 12B, 12C and discharged to a common collection manifold 16. The waste anesthetic gas collection manifold 16 is typically hard plumbed into the healthcare facility, and the anesthetizing machines 12A, 12B, 12C are removably connected to the collection manifold 16 at standard waste anesthetic gas connectors 18A, 18B, 18C, e.g. 19 mm or 30 mm anesthetic connectors. The waste anesthetic gas reclamation system 10 operates at a vacuum pressure which is generated by one or more central vacuum pumps 20. The collected waste gas stream is typically passed through a check valve 35 to a condenser unit 22 consisting of one or more heat exchangers. A source of liquid oxygen, or other suitable heat sink, extracts heat from the waste anesthetic stream, condensing the anesthetic gas components. The liquid waste anesthetic condensate is captured in collection vessels 24, and any liquid water condensate is captured in collection vessel 23. The remaining gas stream, stripped of waste anesthetic gas components, passes through a receiver 26 and the vacuum pump(s) 20, and it is then exhausted to the atmosphere outside of the healthcare facility through vent 46.

The current methods for scavenging waste anesthetic gases from anesthetizing locations 15A, 15B, 15C in healthcare facilities generally involve drawing high flows of room air into the dedicated or shared vacuum collection manifold 16 to entrain waste anesthetic gases. The collection manifold 16 may also continuously draw in air through a number of idle anesthetizing machines 12A, 12B, 12C. On average, the collection system manifold 16 extracts between 20-30 liters of waste anesthetic gas and/or room air per minute at each anesthetizing location 15A, 15B, 15C. For a large hospital having between 20-30 operating rooms, it is estimated that waste anesthetic reclamation system 10 flow rate ranges between 500-1000 /min. (14-35 scf/min.).

The advantages of a high-flow dilute waste gas system are that the system easily accommodates a wide range of anesthetic exhaust flows, the system is safer because little anesthetic can escape the system, and the system is more trouble-free because little maintenance is required. However, high-flow systems are energy-intensive, generally requiring large vacuum pumps 20 in order to maintain sufficient suction at a large number of anesthetizing stations 15A, 15B, 15C. For example, in order to maintain a vacuum of about 200 mm Hg at a flow rate of 1-2 cubic feet per minute (cfm) at each anesthetizing station 15A, 15B, 15C, vacuum pumps of 100-200 cfm capacity are not uncommon.

Additionally, a diluted waste anesthetic gas stream is thermally inefficient. Removal of a waste gas component by condensation requires lowering the temperature of the entire flow stream to a point where the partial pressure of the gaseous waste component is equal to or greater than its saturated vapor pressure (at that temperature). Therefore, to cool the large volume of diluted waste anesthetic gas to a temperature below the saturated vapor pressure of its components, a sizeable cooling utility (i.e. a greater quantity of liquid oxygen, liquid nitrogen, etc.) is required. A method and system for increasing the efficacy and efficiency of condensation-type waste anesthetic gas scavenging and reclamation systems are thus desirable.

A low-flow scavenging system provides a more efficient means of waste anesthetic gas recovery through condensation, because a smaller volume of gas has to be cooled to the condensation temperatures of the individual gases. A low flow scavenging method, facilitated by a dynamic waste anesthetic gas collection apparatus, has recently been disclosed by Berry et al. in co-pending application Ser. No. 11/266,966, entitled "Method of Low Flow Anesthetic Gas Scavenging and Dynamic Collection Apparatus Therefor." This co-pending application, filed on Nov. 4, 2005, is incorporated herein by reference.

Typically, anesthetic gases are highly volatile substances. For a given temperature, they have a higher vapor pressure than the vapor pressure of water and other lower volatile substances. Substances with higher vapor pressures generally require greater cooling to achieve the same or similar condensate recovery as substances with lower vapor pressures. Thus, anesthetic gases need to be cooled to extremely low temperatures, i.e. cryogenic temperatures, in order to recover appreciable amounts of anesthetic as condensate. However, these extremely low temperatures approach, and in many cases, fall below the freeze point of many anesthetics. In such situations, the waste anesthetic gas stream may still contain anesthetic concentrations that could be condensed except for the undesirable freezing of the system.

Pressure, in addition to temperature, can greatly influence condensation. A method and apparatus to enhance anesthetic condensation using a compression stage have recently been disclosed by Berry et al. in co-pending application Ser. No. 11/432,152, entitled "Method and Apparatus for Anesthetic Gas Reclamation with Compression Stage." This co-pending application, filed on May 11, 2006, is incorporated herein by reference. Elevating the pressure of the condensation system is advantageous, because it allows condensation to occur at significantly higher temperatures than would otherwise occur at lower operating pressures. This also avoids the risk and problems associated with freezing of the condensate. For these types of vapor/liquid phase equilibrium systems, the most beneficial thermodynamic characteristic is that the pressure has a much larger effect on the dew point of the vapor than the freezing point of the liquid. Thus, the dew point temperature of a typical anesthetic-laden vapor stream increases with increasing pressure while its freezing point temperature stays relatively constant for varying system pressures.

The increased temperature span between the dew point of the vapor and the freeze point of the condensate, due to increases in system pressure, provides greater operational flexibilities for condensation systems. For example, less cryogenic refrigerant is needed to effect the same amount of condensation, because condensation can occur at higher temperatures. Furthermore, if a more complete separation of the anesthetic from the waste gas stream is desired, the system temperature can be lowered while maintaining an elevated pressure. This permits additional anesthetic to be condensed from the vapor phase without the associated risk of condensate freezing. Thus, a strategy may be developed to achieve the optimum separation of anesthetic by simply adjusting the condensation system pressure relative to the condensation system temperature. Of course, the relative refrigeration versus compression costs should also be considered in any cost optimization strategy.

Using a low-flow anesthetic gas collection device and increasing the gas stream pressure prior to condensation improve both the efficacy and efficiency of waste anesthetic gas reclamation, however, these systems must still be integrated with the existing utility infrastructure of the healthcare facility. As previously mentioned, these prior art systems were typically designed for robust anesthetic waste gas removal. For example, the vacuum pumps, ductwork, valves, etc. of these existing waste anesthetic gas removal systems were sized to handle large volumes of entrained room air along with the waste anesthetic gases. Interfacing more efficient anesthetic scavenging components into an oversized waste air handling system does not necessarily yield the best possible results. Thus, a properly designed waste air handling system, sized to manage the expected capacity of waste gases, is also desirable.

Furthermore, the immense growth in the use of anesthesia outside of the traditional hospital setting has created additional challenges. Anesthetic gases used in small office setting must still be properly managed. However, existing waste anesthetic gas scavenging and reclamation used in hospitals are impractical for use in a small office setting because of their sheer size and expense of operation. Most waste anesthetic gases used in small office settings are simply vented to the atmosphere (or to the operating room) with no treatment and/or attempt to recover the valuable anesthetic components. Therefore, a self-contained waste anesthetic gas scavenging and reclamation system, which will provide the same benefits and/or features as the much larger systems used hospitals and other traditional healthcare facilities, is desirable for these small, discrete office settings.

3. Identification of Objects of the Invention

A primary object of the invention is to provide a system and method for removing fluoro-ethers, nitrous oxide, and other volatile halocarbons from waste anesthetic gases from a surgical or other healthcare facility before such gases are vented to the atmosphere.

Another object of the invention is to provide a system and method for substantially preventing atmospheric venting of fluoro-ethers and other volatile halocarbons of waste anesthetic gas while eliminating the need of prior art catalysts, charcoal granules and heating techniques.

Another object of the invention is to provide a system and method which reclaim and allow re-distillation and/or reuse of a large percentage of the nitrous oxide and/or anesthetic halocarbons used in the facility.

Another object of the invention is to provide a system and method for separating various removed nitrous oxide, fluoroethers, and other volatile halocarbon components based on their characteristic bubble and dew points.

Another object of the invention is to provide a flexible system and method for increasing the efficacy and efficiency of condensation-type waste anesthetic scavenging system by operating the system under varying pressures and temperatures.

Another object of the invention is to provide a system and method for reclaiming anesthetic gases from a waste anesthetic gas stream which do not require integration with existing waste anesthetic gas reclamation systems of the healthcare facility.

Another object of the invention is to provide a system and method for reclaiming anesthetic gases from a waste anesthetic gas stream which minimize reliance on the utility infrastructure and supplies of a healthcare facility.

Other objects, features, and advantages of the invention will be apparent to one skilled in the art from the following specification and drawings.

SUMMARY OF THE INVENTION

The objects identified above, as well as other advantages and features, are preferably embodied in a system/method for the removal of nitrous oxide and volatile halocarbon gas components from waste anesthetic gases, which is arranged and designed to require minimal interaction with the utility systems and supplies of a healthcare facility. The condensation-type waste anesthetic gas reclamation system requires only operational power and an atmospheric discharge vent. Thus, the system/method is essentially self-contained and can be easily used in a small surgical center, such as a physician's office, a small animal clinic, or a dental office.

The waste anesthetic gas reclamation system/method employs a small refrigeration unit, which cools an intermediate heat transfer fluid, such as DuPont Suva® 95 or similar low-temperature refrigerant. The heat transfer fluid, cooled to a temperature of approximately −90° C., is subsequently used in a countercurrent heat exchanger/condenser to cool and condense the anesthetic gas components from the waste anesthetic gas stream. Thus, the system/method does not depend on liquid oxygen or liquid nitrogen supplies from the healthcare facility in order to provide the necessary cryogenic cooling to the waste anesthetic gas stream. However, if desired, liquid oxygen and/or liquid nitrogen supplied by the healthcare facility could be used in the heat exchanger/condenser as the intermediate heat transfer fluid.

In a preferred embodiment of the invention, the system/method employs several additional techniques to increase the efficacy and efficiency of the waste anesthetic reclamation process, thereby making the system as flexible and as self-contained as possible.

First, a low-flow scavenging system is used to collect and segregate a patient's exhalation containing the waste anesthetic gases. The low-flow scavenging unit includes a collection chamber, an exhaust valve to selectively isolate the anesthetizing station from the suction of a collection intake when a patient is not exhaling, and associated sensors, circuitry, controls, or mechanisms to operate the exhaust valve. The patient's exhalation, containing the waste anesthetic gases, enters from the anesthetizing machine exhaust into a collection chamber through a standard anesthetic waste gas connector. Located within the collection chamber is a sensitive pressure sensor which is preferably electrically coupled to a solenoid-operated exhaust valve located at the exhaust side of the collection chamber. The pressure measured by the pressure sensor is the difference between the pressure inside the collection chamber and the ambient air pressure. If the pressure within the collection chamber exceeds the ambient air pressure, the increased pressure is detected by the pressure sensor, which causes control circuitry to open the exhaust valve and results in a rapid decrease in collection chamber pressure. As the chamber pressure approaches the ambient air pressure, the pressure sensor detects the pressure drop and causes the exhaust valve to shut. Through this low-flow scavenging system, the amount of room air which is entrained with the patient's breath containing the waste anesthetic gases is minimized thus reducing the required capacity of the subsequent waste anesthetic reclamation system.

Second, the system/method employs a compressor, having one or more compression stages, to elevate the pressure of the waste anesthetic gas stream prior to anesthetic recovery by condensation. Compression of the waste anesthetic gas to a level above atmospheric pressure is advantageous, because the higher pressure essentially elevates the temperature at which saturation and condensation of the anesthetic gas can occur. Thus, compression of the gas above atmospheric pressure allows the same fraction of anesthetic to be removed by condensation at a higher temperature as would otherwise have occurred by condensation at atmospheric pressure and at a lower temperature. Moreover, a greater fraction of anesthetic may be condensed from the vapor phase as the temperature of the compressed waste anesthetic gas is lowered from this higher temperature. A strategy may be developed to achieve the optimum separation of anesthetic by simply manipulating the condensation system pressure relative to the condensation system temperature. Furthermore, energy and cost saving may be possible when the relative refrigeration versus compression costs are factored into the strategy.

In a preferred embodiment of the invention, the compressed waste anesthetic gas is passed through a multi-stage condenser/heat exchanger wherein heat from the waste anesthetic gas stream is exchanged with the intermediate heat transfer fluid cooled by the small refrigeration unit. In the first condenser stage, any water vapor in the waste anesthetic gas stream is condensed and extracted. In subsequent condenser stages, the temperature of the compressed gas stream is reduced to a point where the partial pressure of each gaseous waste component is equal to or greater than its saturated vapor pressure (at that temperature and elevated pressure). At atmospheric pressure, the anesthetics are extracted from the waste gas into their purified components most efficiently at temperatures near their individual freezing points. However, at elevated pressure, the anesthetics are condensed from the anesthetic vapor mixture at higher temperatures than their individual freezing points. The anesthetics condense as a removal liquid or collect as frost on the cooling surfaces of the condenser. Whether the anesthetic gas components condense as a liquid or deposit as a solid depends on the operational temperature and pressure of the condenser/heat exchanger.

After condensation and extraction of the anesthetic gases into their purified components, the remainder of the anesthetic gas is vented to atmosphere. However, in a preferred embodiment, the waste gas stream is passed through an expansion valve to further cool the gas via the Joule-Thompson effect. This may also induce additional condensation of anesthetic components from the waste gas. More preferably, the waste gas stream is passed through a small turbine, which recovers the potential energy of compression and may induce additional condensation.

BRIEF DESCRIPTION OF THE DRAWINGS

The invention is described in detail hereinafter on the basis of the embodiments represented in the accompanying figures, in which.

DESCRIPTION OF THE PREFERRED EMBODIMENT OF THE INVENTION

The waste anesthetic gas reclamation system is arranged and designed to operate with minimal reliance on the utility infrastructure and supplies of a healthcare facility. Unlike other systems which require liquid oxygen and/or liquid nitrogen supplied by the healthcare facility to condense the gaseous anesthetic components, the system disclosed herein requires only the availability of mechanical or electrical power for operation. Moreover, the present system simply needs an atmospheric vent to discharge the waste gases void of their anesthetic components and does not need an extensive waste air handling system. Thus, the preferred embodiment is comparatively self-contained and can be easily accommodated within a physician's office, veterinary clinic, or dental office. Larger, more conventional waste anesthetic gas reclamation systems, such as those traditionally used in hospitals, would be impractical in these settings because of their sheer size and expense.

Figure 2:
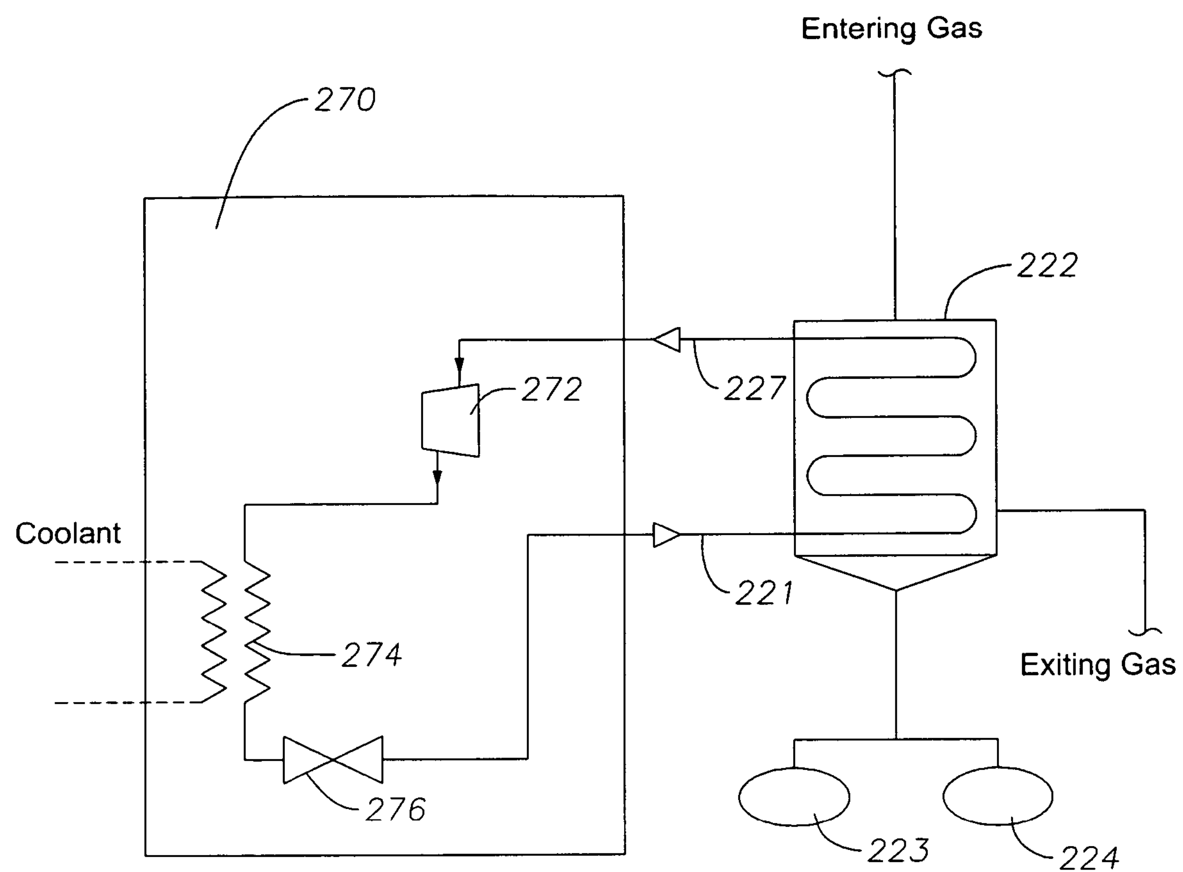
FIG. 2 illustrates in schematic form the heat exchanger/condenser of a preferred embodiment of the invention which cools and condenses anesthetic gas components from the waste anesthetic gas stream through countercurrent heat exchange with an intermediate heat transfer fluid that is cooled in a small refrigeration unit.

FIG. 2 illustrates the heat exchanger/condenser 222 of a preferred embodiment of the invention which cools and condenses anesthetic gas components from the waste anesthetic gas stream through countercurrent heat exchange with an intermediate heat transfer fluid. The heat transfer fluid, such as DuPont Suva® 95 or a similar ultra-low temperature refrigerant, is subsequently cooled using a conventional, electrically or mechanically powered refrigeration unit 270 prior to being returned to the heat exchanger/condenser 222. The use of a separate refrigeration unit 270 to cool a heat transfer fluid or refrigerant eliminates the need for liquid nitrogen and/or liquid oxygen to be supplied by the healthcare facility. DuPont Suva® 95 is the preferred refrigerant, because it is the industry standard for use in medical freezers and other very low temperature applications (between −40° C. and −101° C.), has significantly lower compressor discharge temperatures which allow greater system reliability and compressor longevity, and is an environmentally friendly refrigerant.

As shown in FIG. 2, the heat transfer fluid flows through coils 236 of heat exchanger/condenser 222 and evaporates as it absorbs heat from the anesthetic gas components condensing on the outer surface of coils 236. The intermediate heat transfer fluid is then cooled through a conventional vapor-compression process using a one or more refrigeration stages. The saturated (or slightly superheated) heat transfer fluid, now at least partially evaporated, is compressed in a compressor 272 to a higher pressure. The compression causes the heat transfer fluid to become superheated (i.e. achieve a higher temperature than the saturation temperature of the fluid at the elevated pressure) at the outlet of the compressor 272. The superheated fluid is subsequently cooled and condensed in a heat exchanger/condenser 274 using a suitable coolant, preferably air. The condensed fluid at elevated pressure is then throttled through an expansion valve 276 to a lower pressure. At this point, the heat transfer fluid, consisting mainly of liquid and low quality vapor, is once again ready to absorb heat from the condensing anesthetic gas components in the heat exchanger/condenser 222.

As an alternative to conventional refrigeration systems, a cryogenic refrigeration unit (not shown) may be used to cool an intermediate heat transfer fluid to even lower temperatures (i.e. well below −73° C.) than can be achieved with conventional refrigeration systems. To effect condensation in gaseous anesthetic components with very high vapor pressures (i.e. anesthetics having freezing points below −73° C.), a cryogenically-cooled heat transfer fluid is used to cool and condense these anesthetic components as previously disclosed. Cryogenic refrigeration processes, such as the simple Linde or Joule-Thompson cycle, are well known in the prior art and will not be further discussed herein.

Figure 1:
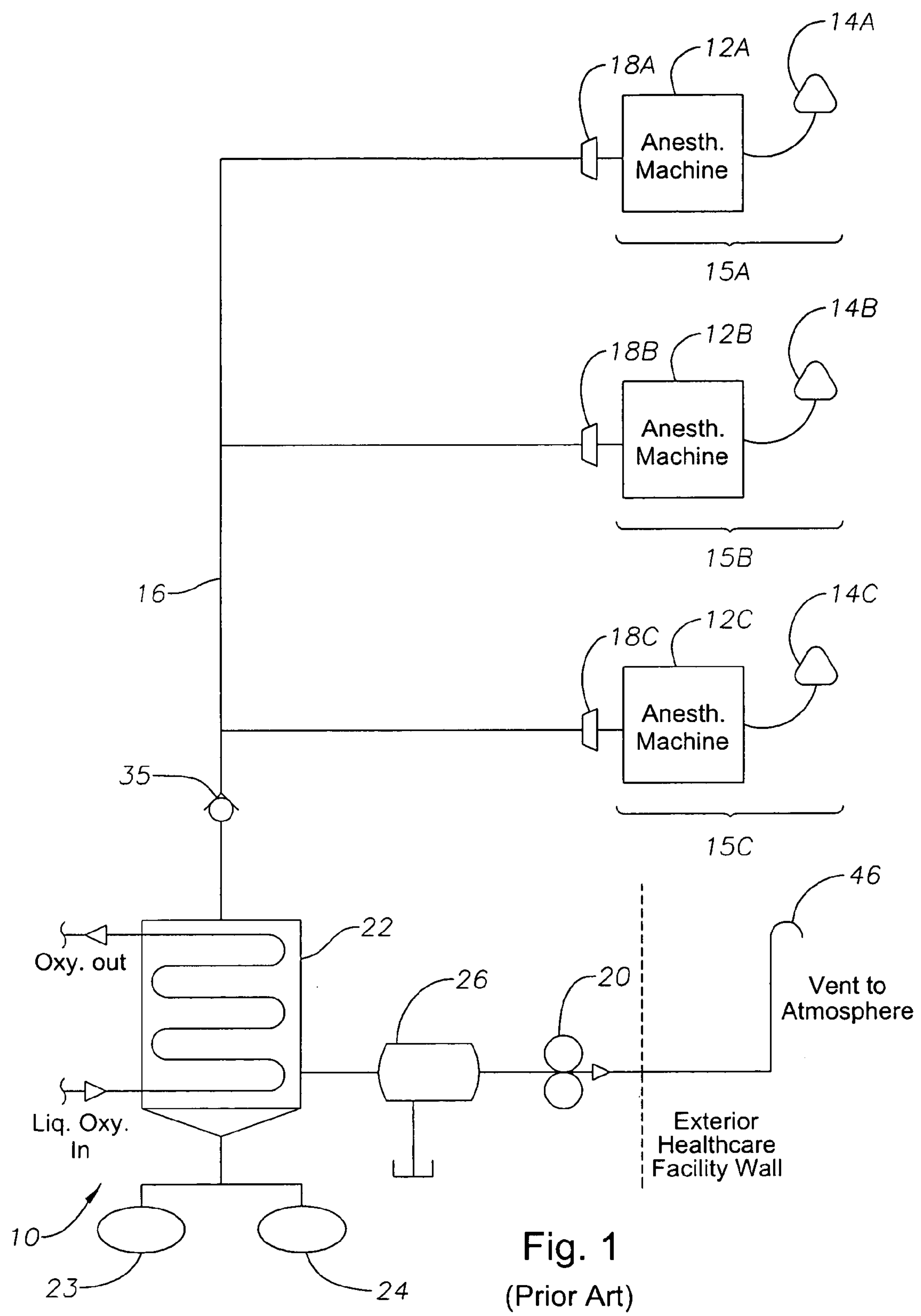
FIG. 1 illustrates in schematic form a high-flow waste anesthetic gas scavenging and reclamation system of prior art by which fluoro-ethers and other volatile anesthetic gas components are separated from the collected gas stream by condensation before the waste gas stream is vented to the atmosphere.
Figure 3:
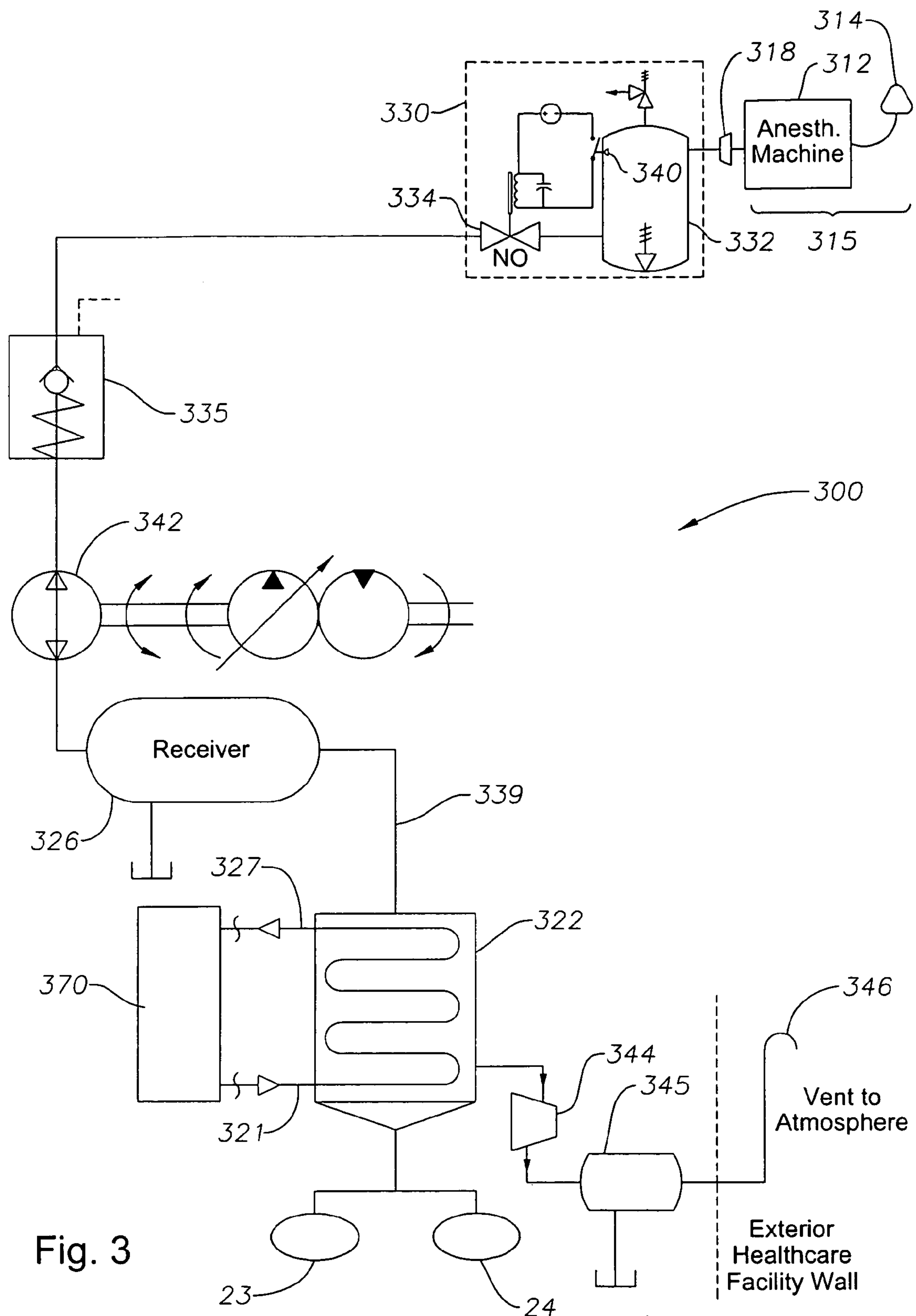
FIG. 3 illustrates in schematic form a preferred embodiment of the anesthetic gas reclamation system which includes a low-flow waste anesthetic gas scavenging unit, a compressor consisting of one or more compression stages, a single or multiple stage condenser/heat exchanger unit to remove the anesthetic gas components from the waste anesthetic gas stream, a small refrigeration unit used to cool the heat transfer fluid used as a refrigerant in the condenser, and a small turbine to capture the potential energy of the compressed waste gas prior to atmospheric venting.

FIG. 3 illustrates a low-flow waste anesthetic gas collection and reclamation system 300 according to a preferred embodiment of the invention for use in a physician's office, dental office, small animal clinic or other healthcare facility. The reclamation system 300 is similar to the previously described prior art waste anesthetic gas reclamation system 10 of FIG. 1 except for the inclusion of a small turbine 344, one or more compression stages provided by a compressor 342, and intelligent waste anesthetic gas collection unit 330 located at or near an anesthetizing station 315 in the healthcare facility.

Compressor 342 is preferably disposed between the intelligent waste anesthetic gas collection unit 330 and the condenser 322. Small turbine 344 is preferably disposed between the condenser 322 and the atmospheric vent 346.

As disclosed in co-pending application Ser. No. 11/266,966 by Berry, the intelligent waste anesthetic gas collection unit 330 is preferably fluidly coupled to the collection intake 316 near the standard waste anesthetic gas connector 318. The intelligent gas collection unit 330 includes a collection chamber 332, an exhaust valve 334 to selectively isolate the suction of the collection intake 316 at the respective anesthetizing station when waste anesthetic gas is not being produced, and associated pressure sensor 340, circuitry, controls, or mechanisms to operate the exhaust valve 334. The collection chamber 332 may be rigid, flexible (such as an elastic bag), or a combination of both.

Referring to FIG. 3, waste anesthetic gas enters from the anesthetizing machine 312 exhaust into chamber 332 through a 19 mm, 30 mm, or similar standard anesthetic waste-gas connector 318. Within the chamber 332 is a sensitive pressure sensor 340 electrically coupled to a solenoid-operated exhaust valve 334 located at the exhaust side of the chamber 332. The pressure measured by pressure sensor 340 is the difference between the pressure of chamber 332 and the outside (ambient) air pressure. If the pressure within the chamber 332 rises to slightly above ambient, the increased pressure is detected by the pressure sensor 340 which by control circuitry causes the exhaust valve 334 to open. Opening valve 334 fluidly connects the chamber 332 to the vacuum source in collection intake 316, resulting in a rapid decrease in pressure in chamber 332. As the chamber pressure approaches ambient, the sensor 340 detects the pressure drop and causes the exhaust valve 334 to close.

The waste anesthetic gas collection intake 316 operates at a slight vacuum pressure, e.g. 5 cm, which is generated by compressor 342. If a compressor 342 is not used in system 300, then a vacuum pump (not shown) will need to be disposed between collection intake 316 and atmospheric vent 346 in order to generate the slight vacuum pressure in collection intake 316. Preventing the collection intake 316 from entraining room air when no waste anesthetic gas is being produced reduces the average anesthetic scavenging flow by approximately 90 percent and subsequently reduces the necessary capacity of the compressor 342, heat exchanger/condenser 322, piping, and other associated hardware (not shown). For a large hospital having between 20-30 operating rooms, it is estimated that waste anesthetic gas flow rate of 500-1000 l/min can be expected using the prior art reclamation system 10 of FIG. 1. A low-flow scavenging system would reduce this anesthetic gas flow rate to 50-100 l/min. The system 300 shown in FIG. 3, for implementation in smaller healthcare facilities, is designed for an anesthetic gas flow rate of 1-20 l/min. Nevertheless, a low-flow scavenging system provides a more efficient means of waste anesthetic gas recovery through condensation whatever the anesthetic gas flow rate, because a smaller volume of gas has to be cooled to the condensation temperatures of the individual anesthetic gases.

From the collection intake 316, the collected waste gas stream is passed through a check valve 335 to a compressor unit 342. In a preferred embodiment, the compressor 342 is sized to compress the anesthetic waste gas from the collection unit 330 to a pressure above atmospheric pressure for subsequent treatment in a condensation unit 322. Pressures above 50 psig are preferable in order to take advantage of attendant increases in separation efficiency and fractional extraction. Multistage compressors are used to avoid the problems associated with high compression ratios, such as high discharge temperatures and increased mechanical breakdowns. As a result, compressor manufacturers recommend a compression ratio of no more than 10:1, especially for low-temperature applications. Multistage compressors can also be more economical than single stage compressors because of the attendant power cost savings attributable to compression stages having smaller compression ratios. However, the compressor 342 of system 300 needs only a single compression stage, because a compression ratio of no more than 10:1 is anticipated.

After compression, the waste anesthetic gas flows through a collection vessel or receiver 326 which allows any liquid condensed due to compression to be removed and separated from the compressed waste anesthetic gas stream. Prior to condensation recovery of the anesthetic components, any water vapor in the gas stream should be removed to prevent freezing of the liquid water condensate in the condenser 322. A preferred method to remove water vapor from the waste anesthetic gas stream is to use a first condenser stage 422A (FIG. 4), however, alternative water removal processes (not shown) may be employed, such as desiccation, adsorption, filtration, semi-permeable or hydrophobic membranes, etc. These various gas drying methods may be used at any point prior to the condensation of the anesthetic gases, including before the compression stage.

Figure 4:
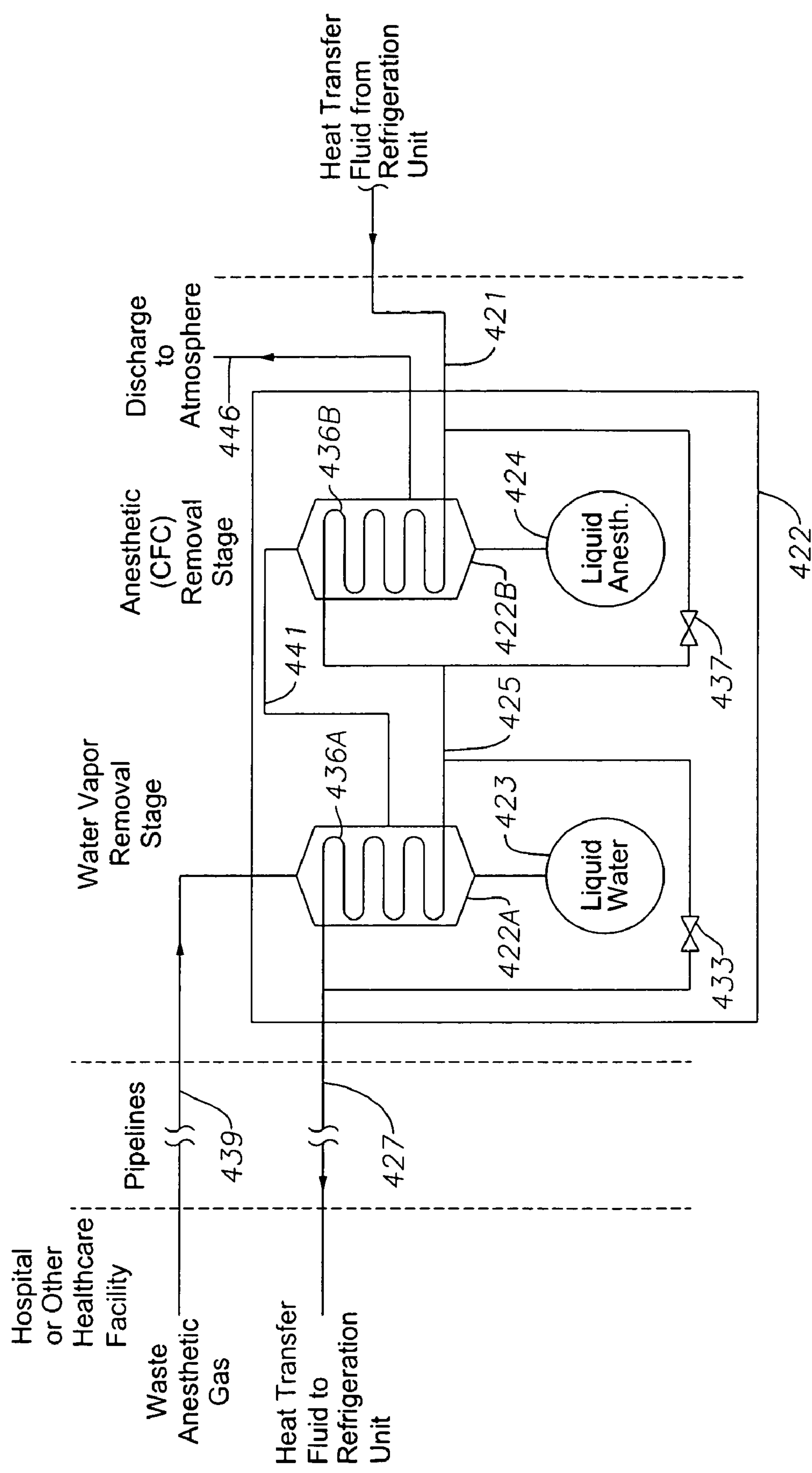
FIG. 4 illustrates in schematic form the process and system by which halocarbon gas components of waste anesthetic gases are liquefied using an intermediate heat transfer fluid to condense those gas components prior to venting of the waste anesthetic gases to the atmosphere.
Figure 5:
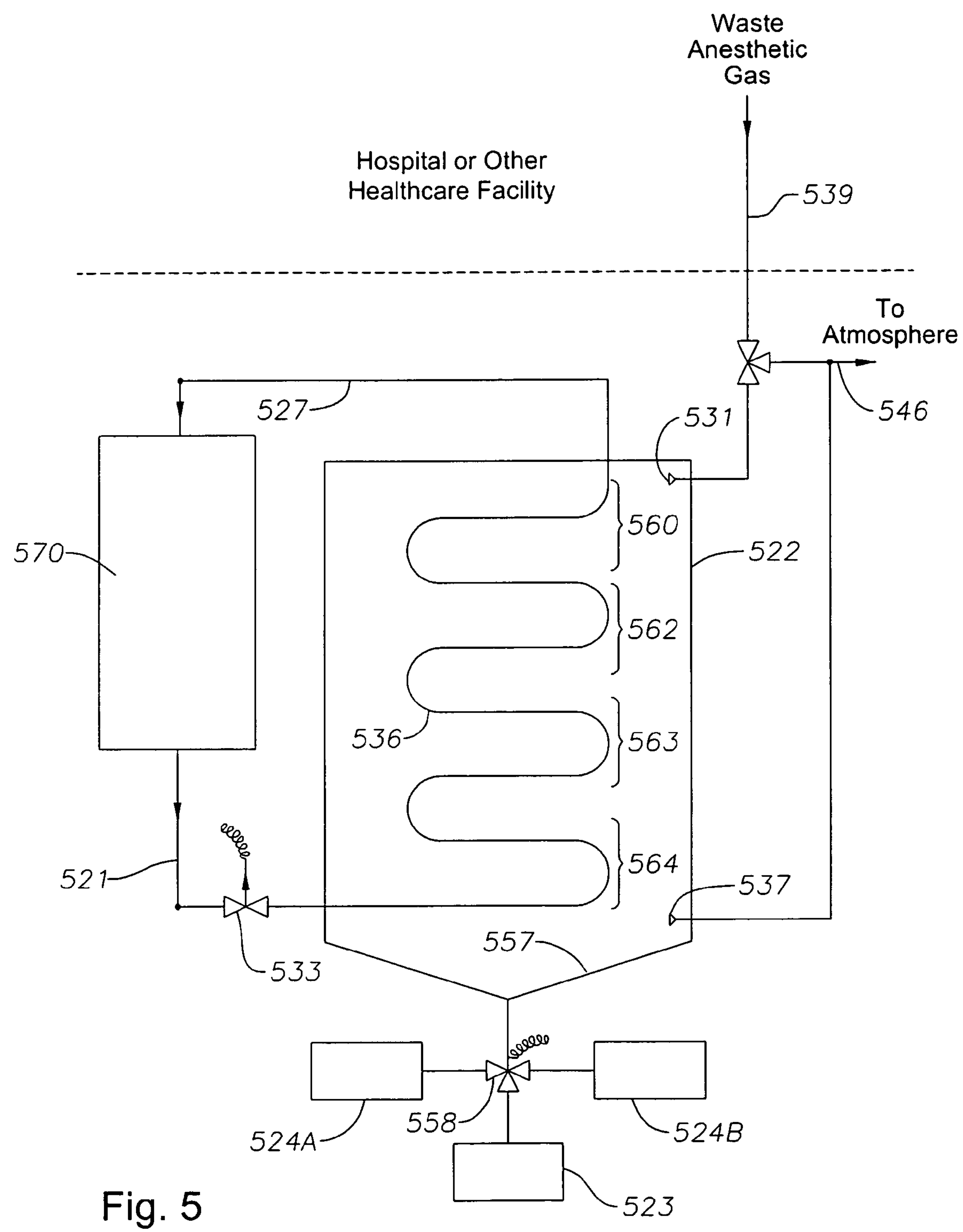
FIG. 5 illustrates in schematic form the process and system by which fluoro-ethers and other volatile halocarbon gas components of waste anesthetic gases are separated therefrom and subsequently fractionated by sequential thawing and collection of the resultant liquid halocarbon prior to venting of the waste anesthetic gases to atmosphere, using as a heat sink for the process a heat transfer fluid cooled in a separate refrigeration unit.

The compressed waste anesthetic gas stream is then cooled in a single or multiple stage condenser 322 such that the temperature of the nitrous oxide and other anesthetic halocarbons are lowered to a point where the vapors either condense on the condenser coils 436B (FIG. 4) as a removal liquid or collect as frost on the condenser coils 536 (FIG. 5). The temperature and pressure at which the condensation process is conducted controls whether the anesthetic gas components are condensed as a removable liquid or deposit as a frost. For the system 300 shown in FIG. 3, a condenser 322 with at least two stages 422A, 422B (FIG. 4) is preferred. The first stage 422A (FIG. 4) is used to remove water vapor from the waste anesthetic gas stream while subsequent stages 422B (FIG. 4) are used to condense the anesthetics. The liquid anesthetic condensates (un-fractionated) are collected in container 324 and the liquid water condensate is collected in container 323, both of which are regularly drained.

A dedicated heat transfer fluid, which flows through the coils 436A, 436B, 536 of condenser 322, is used to cool and condense the anesthetic waste gas components. The heat transfer fluid, such as DuPont Suva® 95 or a similar ultra-low temperature refrigerant, is subsequently cooled using a conventional, electrically powered refrigeration unit 370 prior to being returned to the heat exchanger/condenser 322. As previously disclosed and illustrated in FIG. 2, the intermediate heat transfer fluid is cooled through a conventional vapor-compression process using a one or more refrigeration stages. The use of a separate refrigeration unit 370 to cool a heat transfer fluid or refrigerant eliminates the need for liquid nitrogen and/or liquid oxygen to be supplied by the healthcare facility. However, liquid oxygen, liquid nitrogen, or a similar refrigerant obtained from the common supply of these liquefied gases normally available at a hospital or other medical, dental, or veterinary facility could be used in place of the dedicated heat transfer fluid. If the waste anesthetic gas is compressed above the facility's gas supply pressure (e.g. 50 psig), then contamination of the common refrigerant supply with waste anesthetic is possible should an internal leak occur within the condenser unit 322. Therefore, when using liquid oxygen, liquid nitrogen, or a similar refrigerant, a separate supply source is recommended for waste anesthetic gas pressures above 50 psig in order to avoid the risk of contaminating the common gas supplies of the healthcare facility with waste anesthetic gas.

After the anesthetic components are removed through condensation, the remaining waste gas (mainly composed of entrained air) may be vented to the atmosphere 346. More preferably, however, the compressed waste gas is first throttled through a small turbine 344 or similar device prior to atmospheric release 346 in order to capture the potential energy of the compressed waste gas. The captured energy may then be used to power the compressor 342 or supply other energy requirements of the method and system. Additional anesthetic components in the waste gas may also be condensed by expansion in the turbine 344. These anesthetic condensates are collected in receiver 345 prior to the atmospheric discharge 346 of the waste gas.

Moreover, prior to atmospheric discharge, heat integration of the cooled waste gas with streams to be cooled may reduce the overall cooling utility of the method and system. For example, compression of the waste anesthetic gas stream causes the temperature of the gas stream to increase. The cooled waste gas stream to be vented 346 could be used to cool this compressed waste anesthetic gas stream prior to condensation in order to reduce the overall refrigerant requirement of the heat exchanger/condenser 322.

Berry discloses two cryogenic methods for recovering volatile halocarbons from waste anesthetic gas. First, and more preferably, U.S. Pat. No. 6,729,329 discloses the use of liquid oxygen to condense anesthetic gas components into recoverable liquid condensates. FIG. 4 generally illustrates the system and method of the '329 patent, which has been modified to accommodate an entering compressed waste anesthetic gas stream as well as the replacement of liquid oxygen by a dedicated heat transfer fluid, such as DuPont Suva® 95 or a similar ultra-low temperature refrigerant. Because the dew point temperature of a typical anesthetic-laden vapor stream increases with increasing pressure, this first recovery method for waste anesthetics is significantly and advantageously affected by the increased pressure of the entering waste anesthetic gas stream.

A condenser unit 422 is provided which includes first and second condensers 422A and 422B. The outlet line 421 for cooled heat transfer fluid from refrigeration unit 270 (FIG. 2) is fluidly connected to the condensing coils 436B of the second vessel 422B. The outlet of condensing coils 436B is fluidly connected via flow line 425 to the inlet of coils 436A of first vessel 422A. The outlet of coils 436A is fluidly connected via flow line 427 to the inlet of small refrigeration unit 270 (FIG. 2).

A flow line 439 connects the waste anesthetic gas flow lines from receiver 326, 626 (FIGS. 3 and 6) of the healthcare facility to an inlet of heat exchanger/condenser 422. The waste anesthetic gas enters heat exchanger/condenser 422 via flow line 439 at an elevated temperature due to compression. The compressed waste anesthetic gas enters at the top or entrance of heat exchanger/condenser 422A and passes downward over coils 436A wherein it exchanges heat with the heat transfer fluid flowing countercurrently through the coils 436A. Water vapor in the compressed waste anesthetic gas condenses to liquid water at a specific temperature (above 0° C.), which is dependent upon the pressure of the compressed waste anesthetic gas stream. The liquid water then falls by gravity to tank 423 for storage and removal.

The cooled compressed gas near the bottom of vessel 422A is conducted via flow line 441 to the top or entrance of heat exchanger/condenser 422B where it is applied at a temperature greater than 0° C. The cooled compressed gas applied to the top of heat exchanger/condenser 422B passes over coils 436B wherein it exchanges heat with the heat transfer fluid flowing countercurrently through the coils 436B. The heat transfer fluid from flow line 421 enters the coils 436B at a temperature of approximately −90° C. and leaves the coils 436B via flow line 425 at an increased temperature. If necessary, an intermediate bypass valve 437 may be provided in line 421 to bring the temperature in line 425 at the inlet of coils 436A to approximately 0° C. The temperature of the compressed waste anesthetic gas from flow line 441 is lowered while passing over the coils 436B such that the halocarbons of the waste gas are liquefied and discharged into a collection tank 424. The remainder of the compressed waste gas, i.e., those components which are not harmful to the atmosphere, are preferably throttled through a small turbine 344 (FIG. 3) to capture the potential energy of the compressed gas. Alternatively, these compressed waste gases may be vented to the atmosphere via flow line 446, throttled through an expansion valve 643 (FIG. 6) to induce additional anesthetic condensation, or subjected to further processing by existing catalytic techniques (not shown).

Second, co-pending application Ser. No. 11/432,189 entitled "Anesthetic Gas Reclamation System and Method," discloses the use of a batch-mode frost fractionation process whereby the temperatures of the individual anesthetic gases are lowered to a point such that they condense and collect as frost on the cooling surfaces of a cold trap/fractionator. The cold trap/fractionator is periodically cycled through a thawing stage, during which the cooling surfaces, caked with frost gas components deposited from the waste anesthetic gas passing thereby, are gently warmed to sequentially separate and collect the trapped components. FIG. 5 generally illustrates the system and method of this co-pending patent application, which has been modified to accommodate an entering compressed waste anesthetic gas stream as well as the replacement of liquid oxygen by a dedicated heat transfer fluid, such as Suva® 95 or a similar ultra-low temperature refrigerant. However, because the freezing point temperature of a typical anesthetic-laden vapor stream remains relatively constant for varying system pressures, this second waste anesthetic recovery method is not as significantly affected by increases in the pressure of the waste anesthetic gas stream.

As shown in FIG. 5, a cold trap/fractionator or condenser unit 522 is provided with cooling coils 536 therein. The outlet line 521 for cooled heat transfer fluid from refrigeration unit 570 is fluidly connected to the condensing coils 536 of cold trap/fractionator 522. The flow of cooled heat transfer fluid at the inlet of the coils 536 is controlled thermostatically by valve 533. The cooled heat transfer fluid from flow line 521 enters the coils 536 at a temperature of approximately −90° C. and leaves the coils 536 at approximately 0° C. The outlet of coils 536 is fluidly connected via flow line 527 to the inlet of the small refrigeration unit 570.

A flow line 539 connects the waste anesthetic gas flow lines from receiver 326, 626 (FIGS. 3 and 6) of the healthcare facility to an inlet 531 of heat exchanger/condenser 522. The temperature of the waste anesthetic gas enters heat exchanger/condenser 522 via flow line 539 at an elevated temperature due to compression. The compressed waste anesthetic gas enters at the top or entrance 531 of heat exchanger/condenser 522 and passes downward over coils 536 wherein it exchanges heat with the heat transfer fluid flowing countercurrently through the coils 536. The waste gas leaves the heat exchanger/condenser 522 through fitting 537 and is purged to the atmosphere via flow line 546.

This countercurrent heat exchanger arrangement results in a temperature gradient where the top of the cold trap/fractionator 522 is the warmest and where the bottom of the cold trap/fractionator 522 is the coldest. The upper region 560 of the cooling coils 536 of the cold trap/fractionator 522 cools the compressed waste anesthetic gas to a temperature of approximately −5° C. to extract water vapor as frost on the coils 536. The middle region 562, 563 of the cooling coils 536 next cools the compressed waste anesthetic gas to a temperature of approximately −60° C. which allows sevoflurane to condense and solidify onto the coils 536. Finally, the lower region 564 extracts nitrous oxide by condensation and solidification at a temperature of approximately −90° C. Alternatively, if heat exchanger/condenser 522 is operated under low pressure (i.e. vacuum pressure), then the anesthetic components may be desublimated/deposited directly onto coils 536 without first entering a liquid phase. Furthermore, if the waste anesthetic gas contains isoflurane (melting point of approximately −103° C.) and/or desflurane (melting point of approximately −108° C.), then a cryogenically cooled heat transfer fluid or liquefied gas, such as liquid oxygen or liquid nitrogen, will be required to condense and solidify these anesthetic components onto the lower region 564 of coils 536.

The remainder of the compressed waste gas, i.e., those components which are not harmful to the atmosphere, are preferably throttled through a small turbine 344 (FIG. 3) to capture the potential energy of the compressed gas. Alternatively, these compressed waste gases may be vented to the atmosphere via flow line 546, throttled through an expansion valve 643 (FIG. 6) to induce additional anesthetic condensation, or subjected to further processing by existing catalytic techniques (not shown).

The cold trap/fractionator 522 is periodically cycled through a thaw process in order to defrost the cooling coils 536. Thawing of coils 536 is effectuated by reducing or prohibiting the flow of heat transfer fluid therethrough by thermostatic control valve 533. This allows the cold trap/fractionator 522 to warm to room temperature through heat transfer with its surroundings at ambient temperature. In an alternative embodiment, another fluid (not shown) may be directed through cooling coils 536 to achieve a controlled thaw.

A funnel-shaped hopper 557 forms the lowest point of heat exchanger/condenser 522 and preferably drains into a 4-way selector valve 558, which in turn is fluidly coupled to anesthetic collection tanks 524A, 524B and a water collection tank 523. As the temperature of the coils 536 increases above approximately −90° C. during the thawing stage, nitrous oxide melts from the lower region 564 of cold trap/fractionator 522 and collects in the hopper 557. Selector valve 558 is concurrently aligned to allow the liquid nitrous oxide to gravity feed into one of the collection tanks 524A, 524B. As the temperature continues to warm above −65° C., sevoflurane (melting point of approximately −67° C. at atmospheric pressure) melts from the middle region 562, 563 of the cooling coils 536 and collects in the hopper 557. Selector valve 558 is concurrently aligned to allow the liquid sevoflurane to gravity feed into a second collection tank 524A, 524B. Likewise, as the cold trap/fractionator 522 continues to warm, the water vapor frost will melt above 0° C. from the upper region 560 and be channeled by selector valve 558 into the water collection tank 523. By this method, the fluoro-ethers are fractionated as they are removed from the waste anesthetic gas.

Figure 6:
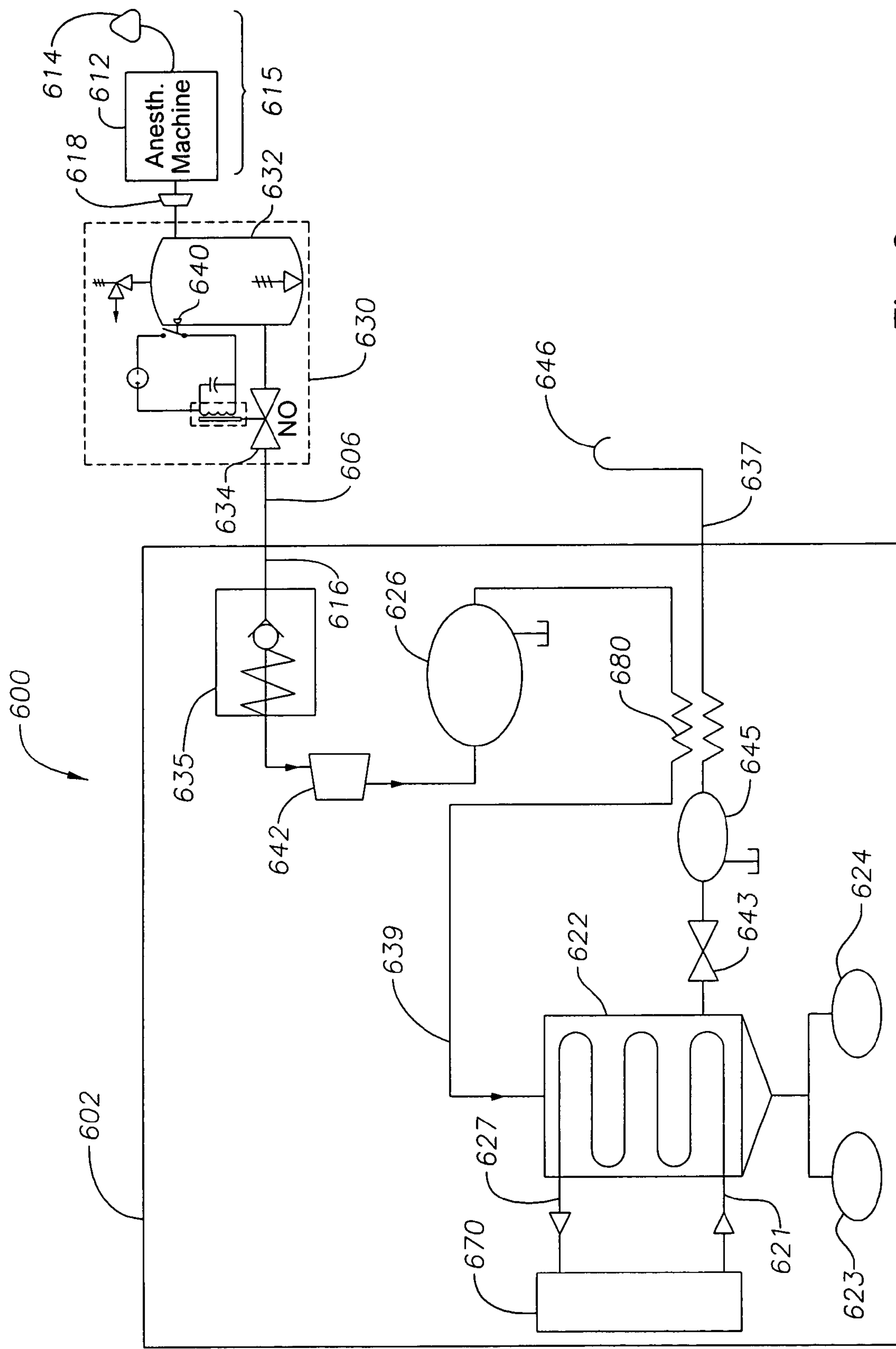
FIG. 6 illustrates in schematic form a preferred embodiment of a self-contained waste anesthetic gas reclamation system which includes a low-flow anesthetic scavenging unit, a compressor, a heat exchanger/condenser to remove the anesthetic gas components from the waste anesthetic gas stream, a small refrigeration unit used to cool the heat transfer fluid used as a refrigerant in the condenser, and an expansion valve to induce additional anesthetic gas condensation.

FIG. 6 illustrates a waste anesthetic gas scavenging and reclamation system 600 according to a preferred embodiment of the invention for use in a physician's office, dental office, small animal clinic or other healthcare facility. The reclamation system 600 is similar to the previously described waste anesthetic gas reclamation system 300 of FIG. 3 in that system 600, like system 300, only requires operational power (not shown), a source flow 615 of anesthetic waste gases, and an atmospheric vent 646. Additionally, however, system 600 is arranged and designed to be a compact, self-contained unit in order to facilitate its placement in a patient's room in proximity with an anesthetizing machine 612. Preferably, system 600 is a packaged unit 602 which occupies a total volume of approximately one cubic foot. System 600 includes a heat exchanger/condenser 622 which cools and condenses anesthetic gas components from the waste anesthetic gas stream through countercurrent heat exchange with an intermediate heat transfer fluid that is cooled in a small refrigeration unit 670. Optionally, system 600 may include a small compressor 642 and receiver 626, and/or an expansion valve 643 (or a small turbine 344 (FIG. 3)) and receiver 645. Additionally, system 600 may incorporate a low-flow anesthetic waste gas collection unit 630.

In a preferred embodiment as shown in FIG. 6, system 600 includes a compressor 642 and receiver 626 as well as an expansion valve 643 and receiver 645. Designed to handle an anesthetic gas flow rate of 1-20 l/min, the waste anesthetic gas collection and reclamation system 600 couples via an attachable flow line 606 to an existing high-flow 615 or more preferably, a low-flow 630 waste anesthetic gas collection unit. The waste anesthetic gas collection intake 616 operates at a slight vacuum pressure, e.g. 5 cm, generated by a compressor 642, which is preferably disposed between intake 616 and the heat exchanger/condenser 622. From collection intake 616, the collected waste gas stream is passed through a check valve 635 to compressor 642. Compressor 642 has a single compression stage sized to elevate the pressure of the anesthetic waste gas from collection unit 615, 630 to a pressure above atmospheric pressure for subsequent treatment in a condensation unit 622.

After compression, the waste anesthetic gas flows through a collection vessel or receiver 626 which allows any liquid condensed due to compression to be removed and separated from the compressed waste anesthetic gas stream. The compressed waste anesthetic gas stream is then cooled in a multistage condenser 622 such that the temperature of the nitrous oxide and other anesthetic halocarbons are lowered to a point where the vapors condense on the condenser coils 436B as a removal liquid (see disclosure with respect to FIG. 4). Alternatively, a single stage condenser 522 (FIG. 5) could be used to condense and collect the vapors as a frost on condenser coils 536 (FIG. 5) (see disclosure with respect to FIG. 5). The temperature and pressure at which the condensation process is conducted controls whether the anesthetic gas components are condensed as a removable liquid or deposited as a frost. For the system 600 shown in FIG. 6, a condenser 622 with at least two stages 422A, 422B (FIG. 4) is preferred. The first stage 422A (FIG. 4) is used to remove water vapor from the waste anesthetic gas stream while the second stage 422B (FIG. 4) is used to condense the anesthetics. The liquid anesthetic condensates (un-fractionated) are collected in small volume (i.e. one liter) container 624 and the liquid water condensate is collected in small volume (i.e. one liter) container 623, both of which are regularly drained.

A dedicated heat transfer fluid, which flows through the coils 436A, 436B, 536 of condenser 622, is used to cool and condense the anesthetic waste gas components. The heat transfer fluid, such as DuPont Suva® 95 or a similar ultra-low temperature refrigerant, is subsequently cooled using a conventional, electrically powered refrigeration unit 670 prior to being returned to the heat exchanger/condenser 622. As previously disclosed and illustrated in FIG. 2, the intermediate heat transfer fluid is cooled through a conventional vapor-compression process using a one or more refrigeration stages.

The use of a separate refrigeration unit 670 to cool a heat transfer fluid or refrigerant eliminates the need for liquid nitrogen and/or liquid oxygen to be supplied by the healthcare facility. However, liquid oxygen, liquid nitrogen, or a similar refrigerant obtained from the common supply of these liquefied gases normally available at a hospital or other medical, dental, or veterinary facility could be used in place of the dedicated heat transfer fluid.

After the anesthetic components are removed through condensation, the remaining compressed waste gases (mainly composed of entrained air) are preferably passed through an expansion valve 643 and a receiver 645 prior to atmospheric venting 646. The expansion valve 643 reduces the compressed waste gas to atmospheric pressure and further cools the waste gas via the Joule-Thompson effect. Additional anesthetic components remaining in the waste gas may be condensed through Joule-Thompson adiabatic expansion. These anesthetic condensates are collected in the receiver 645 prior to the atmospheric discharge 646 of the waste gas.

The cooled waste gas to be vented 646 is then preferably used to cool the entering compressed waste anesthetic gas stream of flow line 639 in a countercurrent heat exchanger 680. This reduces the refrigerant requirement of the heat exchanger/condenser 622, and thus, the overall operational cost of the system 600. The waste gases, throttled through valve 643 and warmed in exchanger 680, are vented through an attachable flow line 637 to an existing atmospheric vent 646 at the healthcare facility.

The Abstract of the disclosure is written solely for providing the United States Patent and Trademark Office and the public at large with a means by which to determine quickly from a cursory inspection the nature and gist of the technical disclosure, and it represents solely a preferred embodiment and is not indicative of the nature of the invention as a whole.

While some embodiments of the invention have been illustrated in detail, the invention is not limited to the embodiments shown; modifications and adaptations of the above embodiment may occur to those skilled in the art. Such modifications and adaptations are in the spirit and scope of the invention as set forth herein.

The invention claimed is:

1. A method of removing and separating gaseous anesthetics from a waste anesthetic gas stream to prevent atmospheric venting of gaseous anesthetics from a healthcare facility, said method comprising the steps of:

receiving said waste anesthetic gas stream from an anesthetizing machine (312, 612) into a chamber (332, 632), detecting a presence of said waste anesthetic gas stream received in said chamber, periodically fluidly coupling said chamber to a collection intake (316, 616) by a selectively isolable flow path (334, 634) in response to said presence of said waste anesthetic gas stream received in said chamber, transferring said waste anesthetic gas stream received in said chamber to said collection intake by said selectively isolable flow path, whereby said chamber and said selectively isolable flow path cooperate to minimize ingress of atmospheric gas into said collection intake when no waste anesthetic gas stream is exiting said anesthetizing machine, cooling said waste anesthetic gas stream transferred to said collection intake by passing said waste anesthetic gas stream over a cooling surface (236, 436A, 436B, 536) characterized by a surface temperature gradient such that said waste anesthetic gas stream passes thereover in a direction from a warmer to a colder temperature, said waste anesthetic gas stream exchanging heat conductively through said cooling surface with a heat transfer fluid, said heat transfer fluid being warmed by said exchange of heat with said waste anesthetic gas stream, said heat transfer fluid being cooled by a refrigeration unit (270, 370, 570, 670), condensing said gaseous anesthetics from said waste anesthetic gas stream, separating said condensed anesthetics from said waste anesthetic gas stream, venting to atmosphere said waste anesthetic gas stream absent said condensed anesthetics.

2. The method of claim 1 further comprising the step of:

compressing said waste anesthetic gas stream to a pressure above atmospheric pressure using a compressor (342, 642) with at least one compression stage.

3. The method of claim 1 wherein said step of condensing said gaseous anesthetics from said waste anesthetic gas stream is conducted at a pressure and temperature to cause said gaseous anesthetics to be condensed as liquids.

4. The method of claim 1 wherein said step of condensing said gaseous anesthetics from said waste anesthetic gas stream is conducted at a pressure and temperature to cause said gaseous anesthetics to be condensed as solids.

5. The method of claim 4 wherein said condensing gaseous anesthetics undergo desublimation onto an outer surface of said cooling surface (236, 536) such that said gaseous anesthetics with a higher desublimation point deposit on a warmer portion (560, 562) of said cooling surface (236, 536) and said gaseous anesthetics with a lower desublimation point deposit on a colder portion (563, 564) of said cooling surface (236, 536).

6. The method of claim 5 further comprising the step of:

heating said cooling surface (236, 536) to selectively remove solid anesthetics thereon as liquid anesthetics such that said liquid anesthetics are sequentially separated and collected based upon melt point temperature.

7. The method of claim 2 further comprising the steps of:

expanding said waste anesthetic gas stream through an expansion valve (643) prior to atmospheric venting thereof, and collecting in a receiver (645) liquefied anesthetic components condensed by expanding said waste anesthetic gas stream through said expansion valve.

8. The method of claim 2 further comprising the steps of:

expanding said waste anesthetic gas stream through a turbine (344) prior to atmospheric venting thereof, and collecting in a receiver (345) liquefied anesthetic components condensed by expanding said waste anesthetic gas stream through said turbine.

9. A system for preventing atmospheric venting of anesthetic gas components of waste anesthetic gas from a healthcare facility, said system comprising:

a chamber (332, 632) for receiving said waste anesthetic gas from an anesthetizing machine (312, 612), a detector (340, 640) for detecting a presence of said waste anesthetic gas received in said chamber, an exhaust valve (334, 634) arranged and designed to periodically fluidly couple said chamber to a collection intake (316, 616) in response to said presence of said waste anesthetic gas received in said chamber when detected by said detector, whereby said chamber and said exhaust valve cooperate to minimize ingress of atmospheric gas into said collection intake when no said waste anesthetic gas is exiting said anesthetizing machine, said collection intake (316, 616) arranged and designed to draw said waste anesthetic gas from said chamber via said exhaust valve into a flow line (239, 339, 439, 539, 639), a heat exchanger/condenser (222, 322, 422, 522, 622) arranged and designed to remove said anesthetic gas components from said waste anesthetic gas, said heat exchanger/condenser having an inlet fluidly coupled to said flow line (239, 339, 439, 539, 639) and an outlet fluidly coupled to an atmospheric vent line, said heat exchanger/condenser also having a cooling coil (236, 436A, 436B, 536) positioned therein with an outlet of said cooling coil fluidly coupled to a heat transfer fluid flow line (227, 337, 427, 527, 627), said cooling coil having an inlet and providing a cooling surface characterized by a surface temperature gradient, said heat exchanger/condenser having at least one vessel (224, 324, 424, 524A, 524B, 624) for collecting liquefied anesthetic components removed from said waste anesthetic gas within said heat exchanger/condenser, and a refrigeration unit (270, 370, 570, 670) having an inlet fluidly coupled to said heat transfer fluid flow line (227, 327, 427, 527, 627) from said outlet of said cooling coil and an outlet fluidly coupled via another heat transfer fluid flow line (221, 321, 421, 521, 621) to said inlet of said cooling coil, said refrigeration unit for cooling a heat transfer fluid flowing through said cooling coil.

10. The system of claim 9 wherein said refrigeration unit (270, 370, 570, 670) further comprises:

a compressor (272) for compressing said heat transfer fluid, a heat exchanger (274), said heat exchanger using a coolant to cool said compressed heat transfer fluid, and an expansion valve (276) for decompressing said heat transfer fluid.

11. The system of claim 9 wherein said heat exchanger/condenser (222, 322, 422, 522, 622) further comprises:

a first heat exchanger/condenser stage (422A) having an inlet fluidly coupled to said flow line (239, 339, 439, 539, 639) and an outlet, said first heat exchanger/condenser stage having a first cooling coil (436A) positioned therein with an outlet of said first cooling coil fluidly coupled to said heat transfer fluid flow line (227, 327, 427, 527, 627) to said refrigeration unit (270, 370, 570, 670), said first cooling coil (436A) having an inlet, and a second heat exchanger/condenser stage (422B) having an inlet which is fluidly coupled to said outlet of said first heat exchanger/condenser stage (422A) and an outlet fluidly coupled to said atmospheric vent line, said second heat exchanger/condenser stage also having a second cooling coil (436B) positioned therein with an outlet of said second cooling coil fluidly coupled to said inlet of said first cooling coil (436A) and an inlet of said second cooling coil fluidly coupled to said another heat transfer fluid flow line (221, 321, 421, 521, 621) from said refrigeration unit (270, 370, 570, 670).

12. The system of claim 9 further comprising:

a compressor (342, 642) having at least one compression stage for elevating said waste anesthetic gas to a pressure higher than atmospheric pressure.

13. The system of claim 12 further comprising:

an expansion valve (643) fluidly coupled to said outlet of said heat exchanger/condenser (222, 322, 422, 522, 622), said expansion valve (643) for reducing pressure of waste gas to be vented, and a receiver (645) fluidly coupled between said expansion valve (643) and said atmospheric vent line (646), said receiver (645) for collecting liquefied anesthetic components condensed by reducing said pressure of said waste gas.

14. The system of claim 12 further comprising:

a turbine (344) fluidly coupled to said outlet of said heat exchanger/condenser (222, 322, 422, 522, 622), said turbine (344) for reducing pressure of waste gas to be vented, and a receiver (345) fluidly coupled between said turbine (344) and said atmospheric vent line (346), said receiver (345) for collecting liquefied anesthetic components condensed by reducing said pressure of said waste gas.

15. A system for preventing atmospheric venting of anesthetic gas components of waste anesthetic gas from a healthcare facility, said system comprising:

a chamber (332, 632) for receiving said waste anesthetic gas from an anesthetizing machine (312, 612), a detector (340, 640) for detecting any presence of said waste anesthetic gas received in said chamber, an exhaust valve (334, 634) arranged and designed to periodically fluidly couple said chamber to a collection intake (316, 616) in response to said presence of said waste anesthetic gas received in said chamber when detected by said detector, whereby said chamber and said exhaust valve cooperate to minimize ingress of atmospheric gas into said collection intake when no said waste anesthetic gas is exiting said anesthetizing machine, said collection intake (316, 616) arranged and designed to receive said waste anesthetic gas from said chamber via said exhaust valve, said collection intake fluidly coupled to a flow line (239, 339, 439, 539, 639), a first stage (422A) of a heat exchanger/condenser (222, 322, 422, 522, 622) having an inlet fluidly coupled to said flow line (239, 339, 439, 539, 639) and an outlet, said first stage also having a first cooling coil (436A) positioned therein with an outlet of said first cooling coil fluidly coupled to a heat transfer fluid flow line (227, 327, 427, 527, 627), said first cooling coil (436A) having an inlet, a second stage (422B) of said heat exchanger/condenser (222, 322, 422, 522, 622) having an inlet fluidly coupled to said outlet of said first stage (422A) and an outlet fluidly coupled to an atmospheric vent line, said second stage having a second cooling coil (436B) positioned therein with an outlet of said second cooling coil fluidly coupled to said inlet of said first cooling coil (436A) and an inlet, said first and second cooling coils providing a cooling surface characterized by a surface temperature gradient, said heat exchanger/condenser arranged and designed to remove said anesthetic gas components from said waste anesthetic gas, said heat exchanger/condenser having at least one vessel (224, 324, 424, 524A, 524B, 624) for collecting liquefied anesthetic components removed from said waste anesthetic gas within said heat exchanger/condenser, and a refrigeration unit (270, 370, 570, 670) having an inlet fluidly coupled to said heat transfer fluid flow line (227, 327, 427, 527, 627) from said outlet of said first cooling coil and an outlet fluidly coupled via another heat transfer fluid flow line (221, 321, 421, 521, 621) to said inlet of said second cooling coil, said refrigeration unit for cooling a heat transfer fluid flowing through said first and second cooling coils.

16. The system of claim 15 further comprising:

a compressor (342, 642) having at least one compression stage for elevating said waste anesthetic gas to a pressure higher than atmospheric pressure.

17. The system of claim 16 further comprising:

an expansion valve (643) fluidly coupled to said outlet of said second stage (422B) of said heat exchanger/condenser (222, 322, 422, 522, 622), said expansion valve (643) for reducing pressure of waste gas to be vented, and a receiver (645) fluidly coupled between said expansion valve (643) and said atmospheric vent line (646), said receiver (645) for collecting liquefied anesthetic components condensed by reducing said pressure of said waste gas.

18. The system of claim 16 further comprising:

a turbine (344) fluidly coupled to said outlet of said second stage (422B) of said heat exchanger/condenser (222, 322, 422, 522, 622), said turbine (344) for reducing pressure of waste gas to be vented, and a receiver (345) fluidly coupled between said turbine (344) and said atmospheric vent line (346), said receiver (345) for collecting liquefied anesthetic components condensed by reducing said pressure of said waste gas.

19. The method of claim 1 wherein said step of condensing said gaseous anesthetics from said waste anesthetic gas stream is conducted at a pressure and temperature to cause at least one of said gaseous anesthetics to be condensed as a solid.

20. The system of claim 15 wherein said refrigeration unit (270, 370, 570, 670) further comprises:

a compressor (272) for compressing said heat transfer fluid, a heat exchanger (274), said heat exchanger using a coolant to cool said compressed heat transfer fluid, and an expansion valve (276) for decompressing said heat transfer fluid.

* * * * *